United States Patent [19]

Kurata et al.

[11] 4,204,915
[45] May 27, 1980

[54] PROCESS FOR AZEOTROPIC DISTILLATION

[75] Inventors: Kenzi Kurata, Iwakuni; Toshito Fukumoto, Otake; Yuji Yoshida, Iwakuni; Masanori Kusama, Otake; Shintaro Tsuruta, Iwakuni, all of Japan

[73] Assignee: Mitsui Petrochemical Industries, Ltd., Tokyo, Japan

[21] Appl. No.: 887,609

[22] Filed: Mar. 17, 1978

[30] Foreign Application Priority Data

Mar. 19, 1977 [JP] Japan .................................. 52/29783

[51] Int. Cl.$^2$ .......................... B01D 3/36; B01D 3/42; C07C 51/46; C07C 29/28
[52] U.S. Cl. .......................................... 203/2; 203/50; 203/60; 203/67; 203/68; 203/69; 203/70; 203/DIG. 23
[58] Field of Search .................. 203/2, 60, 69, 67, 57, 203/50, 68, 70, DIG. 23, 14–19; 202/160; 562/608; 568/913

[56] References Cited

U.S. PATENT DOCUMENTS

| 1,568,349 | 1/1926 | Steffens | 203/18 |
|---|---|---|---|
| 1,860,512 | 5/1932 | Ricard et al. | 203/16 |
| 2,159,146 | 5/1939 | Guinot | 203/16 |
| 2,171,549 | 9/1939 | Gordon et al. | 203/16 |
| 3,050,450 | 8/1972 | Kleiss et al. | 203/2 |
| 3,132,078 | 5/1964 | Backlund | 203/58 |
| 3,293,154 | 12/1966 | Newton | 203/18 |
| 3,431,181 | 3/1969 | Bouniot | 203/18 |
| 3,692,636 | 9/1972 | Huguet | 203/2 |

*Primary Examiner*—Wilbur L. Bascomb, Jr.
*Attorney, Agent, or Firm*—Cooper, Dunham, Clark, Griffin & Moran

[57] ABSTRACT

An azeotropic distillation is conducted by feeding a part of an entrainer to the lower region of an azeotropic zone in a distillation column.

8 Claims, 3 Drawing Figures

PROCESS FOR AZEOTROPIC DISTILLATION

BACKGROUND OF THE INVENTION

1. Field of the Invention

This invention relates to a process for separating a compound from water in a mixture of the compound and water by azeotropic distillation in the presence of an entrainer.

2. Description of the Prior Art

Heretofore, for example, separation of acetic acid from water in the mixture has been effectively effected by azeotropic distillation in the presence of an entrainer, that is, the azeotropic mixture of water and the entrainer is distilled from the top of a fractionating column while dehydrated acetic acid or a concentrated acetic acid is withdrawn from the bottom. This method is disclosed in U.S. Pat. Nos. 1,917,391 and 2,050,234 and British Pat. No. 298,137. This azeotropic distillation has various advantages such as a high efficiency of separation, low reflux ratio and a reduced heat energy required for distillation and the like.

However, according to this azeotropic distillation, the gas-liquid composition distribution in the column is much more complicated than that in a usual distillation, and such distribution is easily changed even by a slight change in quantity, composition, and temperature of the feed, quantity of refluxed entrainer, reflux ratio of the aqueous phase and other operating conditions and therefore, a stable operation of a distillation column is very difficult. For example, a minor change in the operating condition results in adversely affecting the separation efficiency at the top of the column and contamination of a bottom product with the entrainer when a higher boiling entrainer is used. In a usual distillation, when such change in a gas-liquid composition distribution in a distillation column occurs, a stable operation can be carried out by controlling the operation conditions such as reflux ratio, heat energy supplied to a reboiler and the like. However, in case of azeotropic distillation, simple control of the quantity of reflux of the entrainer and heat supply to the reboiler are not sufficient to suppress a change in the gas-liquid composition distribution in the distillation column, in particular a change in the azeotropic zone, further in particular, a change in the lower region of said azeotropic zone where the content of the entrainer in the liquid composition varies to a great extent.

SUMMARY OF THE INVENTION

An object of the present invention is to provide a process for azeotropic distillation where change in the azeotropic zone is suppressed.

Another object of the present invention is to provide a process for azeotropic distillation where the operation of the azeotropic distillation is stabilized.

A further object of the present invention is to provide a process for azeotropic distillation where neither the distillate product nor the bottom product is contaminated with the entrainer.

Still another object of the present invention is to provide a process for azeotropic distillation capable of stably operating a distillation column under a low reflux ratio.

A still further object of the present invention is to provide a process for azeotropic distillation where the amount of the entrainer in the distillation column can be optionally controlled by a simple procedure and there can be suppressed a change in the gas-liquid composition distribution in the azeotropic zone, in particular, in the lower region where the content of the entrainer in the liquid composition varies to a great extent, of the azeotropic zone.

According to the present invention, there is provided a process for separating a compound from water in a mixture of the compound and water by azeotropic distillation in the presence of an entrainer to be refluxed which comprises detecting a temperature change at the lower region of an azeotropic zone, the content of the entrainer in the liquid composition varying to a great extent at the lower region of the azeotropic zone, and feeding a part of the entrainer to the lower region of the azeotropic zone based on the detected temperature change to suppress the change at the azeotropic zone.

DESCRIPTION OF THE PREFERRED EMBODIMENT

Figure 1:
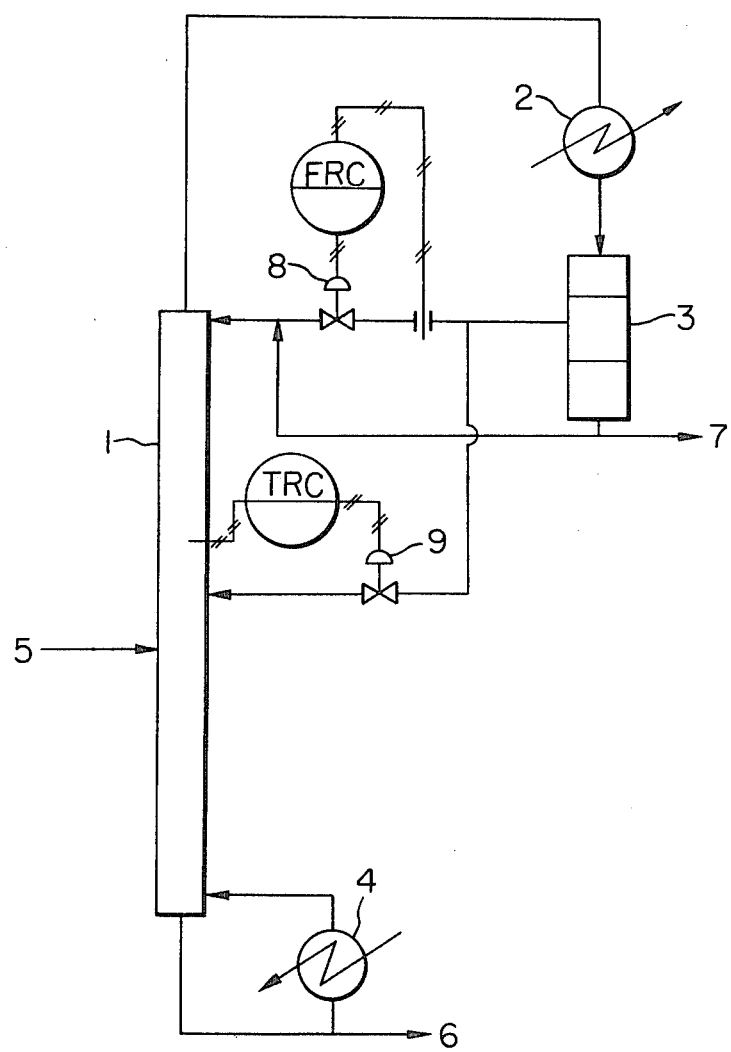
FIG. 1 shows schematically distillation apparatus which may be used for azeotropic distillation according to the present invention.

According to the present invention, the composition of the components, that is, a compound and water, fed to a distillation column is optional.

For example, when the compound is acetic acid, a mixture of acetic acid and water which contains 10–95% by weight of water, preferably, 40–95% by weight of water, may be used.

As an entrainer, there may be employed various entrainers which have been, heretofore, used for azeotropic distillation for a mixture of water and acetic acid. Representative entrainers are esters such as butyl formate, amyl formate, isoamyl formate, allyl acetate, butyl acetate, n-propyl propionate, isopropyl propionate, allyl propionate, butyl propionate, isobutyl propionate, methyl butyrate, ethyl butyrate, propyl butyrate, isopropyl butyrate, and the like, ethers such as dichloromethyl ether, ethyl isoamyl ether, allyl isoamyl ether, ethyl amyl ether, di-n-butyl ether, di-isobutyl ether and the like, halogenated hydrocarbons such as amyl chloride, ethylene dichloride, propylene dichloride, chlorobenzene and the like, ketons such as chloroacetone, ethyl propyl ketone, dipropyl ketone, methyl butyl ketone, methyl isobutyl ketone, allyl acetone, mesityl oxide and the like, aromatic hydrocarbons such as toluene, xylene, ethyl benzene and the like, and other similar compounds having a boiling point of from 100° to 150° C. and capable of forming an azeotropic mixture with water. Among these entrainers, esters are preferable and in particular, butyl acetate is preferable.

Other than the above mentioned distillation involving a heterogeneous azeotropic system for a mixture of water and acetic acid where the azeotropic mixture forms two liquid phases of different composition, there may be mentioned the following heterogeneous azeotropic distillations:

n-butanol-water system where the entrainer may be hexane, cyclohexane, heptane, octane, nonane or the like;
ethanol-water system where the entrainer may be $CS_2$, $CCl_4$, bromoethane, benzene or the like;
propanol-water system where the entrainer may be $CCl_4$, tetrachloroethylene, benzene, toluene, hexane or the like;
methanol-water system where the entrainer may be $CS_2$, benzene, toluene or the like.

The azeotropic distillation can be carried out under atmospheric pressure, elevated pressure or reduced pressure, but usually it is carried out under atmospheric pressure. The azeotropic distillation can be effected either batchwise or continuously.

According to the azeotropic distillation of the present invention, for example, in case of acetic acid-water system, an azeotropic mixture of water and an entrainer is distilled from the top of the column and when the azeotropic mixture is cooled, it is separated into two phases, an aqueous phase and an entrainer phase. One part of the aqueous phase is refluxed to the top of the column, if necessary, and the other part is withdrawn while the entrainer phase is refluxed to the top of the column and to the lower region of the azeotropic zone in the column. From the bottom of the column, dehydrated acetic acid or a concentrated acetic acid is obtained.

The quantity of the entrainer to be refluxed to the top of the column depends upon the composition of the mixture of water and acetic acid, theoretical plate number of the column, type of entrainer, and the operating conditions.

Where an azeotropic distillation of acetic acid and water is effected in the presence of an entrainer according to the present invention, the liquid composition distribution and the temperature distribution in a distillation column are as shown in FIG. 2.

Figure 2B:
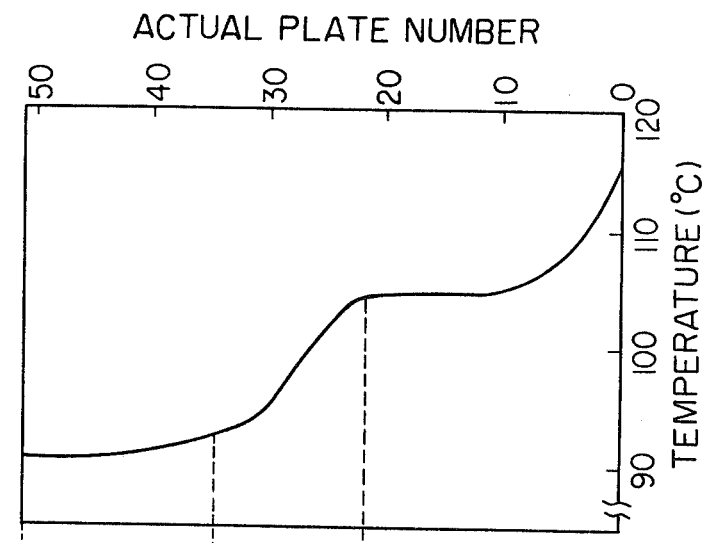
FIG. 2B shows a temperature distribution in a distillation column as mentioned above.
Figure 2A:
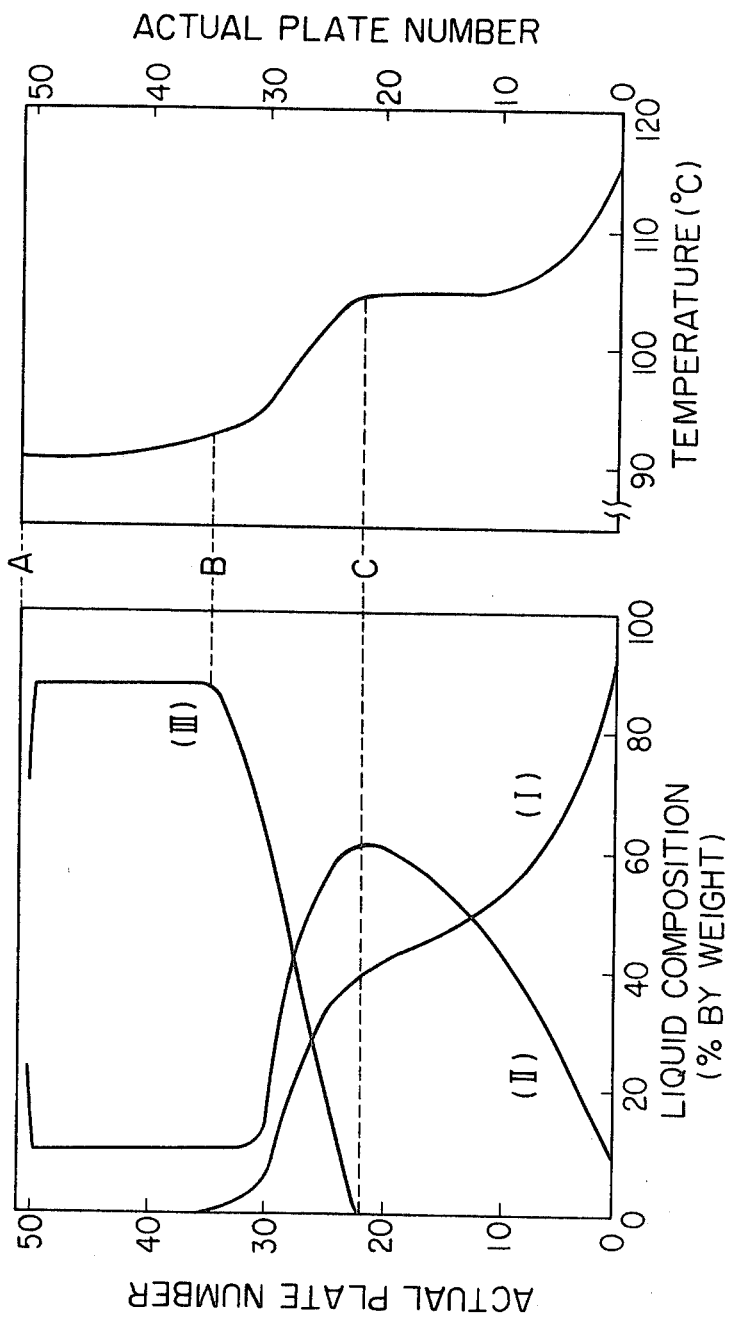
FIG. 2A shows a liquid composition distribution in a distillation column where separation of acetic acid and water is conducted by an azeotropic distillation using butyl acetate as an entrainer.

FIG. 2A shows a liquid composition distribution in a distillation column where a mixture of 43.49% by weight of acetic acid and 56.51% by weight of water is subjected to an azeotropic distillation in the presence of butyl acetate as an entrainer by using a distillation column having 50 actual plate number at a reflux ratio of 0.65 for the aqueous phase, and FIG. 2B shows a temperature distribution in the distillation column.

According to the present invention, the term, "azeotropic zone", means a region in a distillation column where the concentration of an entrainer in a liquid composition is 0.1% by weight or more. For example, the region between A and C in FIG. 2 is an azeotropic zone. At the upper region of this azeotropic zone (between A and B in FIG. 2), variation of content of the entrainer in the liquid composition is a little excluding the uppermost plate while at the lower region of the azeotropic zone (between B and C in FIG. 2), the variation of the content of the entrainer is large and, thereby, change of temperature distribution in the column is also large. As mentioned above, in such azeotropic distillation, vapor-liquid composition distribution in the azeotropic zone, particularly, that at the lower region of the azeotropic zone is changed to a great extent by even a small change of operating conditions such as composition, quantity, and temperature of a feed charged to a distillation column, quantity of reflux of the entrainer, quantity of heat supplied to a reboiler. As the result, the distillation can not be carried out at a stable state. For example, the lower region of the azeotropic zone (between B and C) transfers upward or downward and therefore, the entrainer contaminate the concentrated acetic acid in the bottom product while the separation efficiency of water from acetic acid is lowered at the overhead.

As mentioned above, a large change of temperature distribution in a distillation column is observed at the lower region of the azeotropic zone corresponding to the change of gas-liquid composition distribution and therefore, it is possible to detect the change in the azeotropic zone by measuring the temperature change. As a means for detecting the change in the azeotropic zone, the measurement of temperature change is preferable because it is simple.

As an embodiment of control based on the detected temperature, a temperature controlling valve is used for adjusting the reflux quantity of an entrainer and the quantity of an entrainer fed to the lower region of the azeotropic zone.

The quantity of an entrainer fed to the lower region of the azeotropic zone is controlled based on change of temperature at the lower portion of the azeotropic zone, and a ratio of the quantity of an entrainer fed to the lower region to the quantity of the refluxing entrainer is usually in a range of from 0.01 to 0.50, preferably from 0.01 to 0.20.

The following examples are given for illustrating the present invention, but by no means for limiting the present invention.

EXAMPLE 1

The process of the present invention was carried out by using a continuous distillation apparatus in FIG. 1. As an entrainer, butyl acetate was used and the fractionating column is a ripple tray type column having 50 plates.

At the beginning of the continuous azeotropic distillation, a mixture of 43.49% by weight of acetic acid and 56.51% by weight of water was fed to the column 1 and the distillation was carried out under total reflux, and then butyl acetate was gradually fed to column 1 from a decanter 3 to form a ternary azeotropic system of acetic acid-water-butyl acetate. Then a mixture of 43.49% by weight of acetic acid and 56.51% by weight of water was fed through a feed inlet 5 positioned between the 21st plate and the 22nd plate at a rate of 178.52 Kg./hr. and a concentrated acetic acid was withdrawn as a bottom product at a rate of 83.21 Kg./hr. from a bottom 5 while an aqueous phase in a decanter drum 3 connected to a cooler 2 was withdrawn through a water withdrawing line 7 at a rate of 95.32 Kg./hr. (D), and another portion of the aqueous phase (11.354 Kg./hr.)($R_W$) and an oil phase in decanter drum 3 (272.31 Kg./hr.)($R_o$) were returned to the top of column 1 as reflux to carry out the continuous azeotropic distillation. The flow rate of the oil phase (butyl acetate) as reflux was controlled by a flow rate controlling valve 8. Further, the temperature at the 31st plate of the column (in the lower region of the azeotropic zone as is clear from FIG. 2A and FIG. 2B) was detected and was adjusted to 94° C. by feeding appropriately a part of the oil phase (butyl acetate) in decanter drum 3 to a portion between the 26th plate and the 27th plate through a temperature regulating valve 9. The feed quantity (S) of the oil phase (butyl acetate) at a stable continuous azeotropic distillation operation was 30.45 Kg./hr. and the ratio to the reflux oil phase ($S/R_o$) was 0.1118. Reflux ratio of the aqueous phase, $(R_W + R_o + S)/D$, was 0.65 (molar ratio). FIG. 2A shows the liquid composition distribution in column 1 when the continuous azeotropic distillation reached a constant state. In FIG. 2A, curve (I) denotes acetic acid, curve (II) water and curve (III) butyl acetate, and a temperature distribution in column 1 is shown in FIG. 2B.

This continuous distillation was effected for 9 hours. A temperature at the bottom of column 1 was 114.5±0.1° C., a temperature at the top of column 1 was 90.5±0.1° C. and a temperature at the 31st plate in the lower region of the azeotropic zone was 94.0±0.1° C. These temperatures were very stable and the temperature distribution in column 1 hardly deviates from the temperature distribution curve in FIG. 2B. Content of acetic acid in the concentrated acetic acid withdrawn from the bottom of the column was stably 93.30% by weight while that of water was stably 6.70% by weight, and during the continuation distillation, butyl acetate was not detected at all. Content of acetic acid in the aqueous phase withdrawn from decanter drum 3 was stably 0.007% by weight and that of butyl acetate was also stably 0.50% by weight.

COMPARISON EXAMPLE 1

The operation of Example 1 was repeated except that a part of the oil phase from decanter drum 3 was not fed to a portion between the 26th plate and the 27th plate and therefore, the total quantity (302.76 Kg./hr.) of the oil phase was returned to the top of column 2 as a reflux. As the continuation distillation proceeded, the concentration of acetic acid in the aqueous phase in decanter drum 3 increased and amounted to 7.4% by weight, and the concentration of butyl acetate contained in acetic acid withdrawn from the bottom of column 1 was 0.01% by weight. This result shows that a stable azeotropic distillation can not be effected if a part of the oil phase from decanter drum 3 is not fed to the lower region of the azeotropic zone through a temperature regulating valve.

What we claim is:

1. A process for separating a compound from a mixture of water and the compound which comprises:

(a) distilling the mixture in a distillation column in the presence of an entrainer which forms an azeotrope with the water in an azeotropic zone of the column;
   (b) separating the azeotrope as an overhead fraction;
   (c) condensing the azeotrope to form a water-rich phase and an entrainer-rich phase;
   (d) refluxing a first portion of the entrainer-rich phase into the upper region of the azeotropic zone through a first entrainer feed and a second portion into the lower region of the azeotropic zone through a second entrainer feed;
   (e) detecting the temperature in the lower region of the azeotropic zone; and
   (f) controlling the amount of entrainer refluxed through the second entrainer feed based on the temperature so as to suppress a temperature change in the lower azeotropic zone.

2. A process according to claim 1 where the compound is acetic acid.

3. A process according to claim 2 where the entrainer is an ester having boiling point of from 100° to 150° C.

4. A process according to claim 3 where the ester is butyl acetate.

5. A process according to claim 1 where the compound is n-butanol and the entrainer is selected from the group consisting of hexane, cyclohexane, heptane, octane and nonane.

6. A process according to claim 1 where the compound is ethanol and the entrainer is selected from the group consisting of $CS_2$, $CCl_4$, bromoethane and benzene.

7. A process according to claim 1 where the compound is propanol and the entrainer is selected from the group consisting of $CCl_4$, tetrachloroethylene, benzene, toluene and hexane.

8. A process according to claim 1 where the compound is methanol and the entrainer is selected from the group consisting of $CS_2$, benzene and toluene.

* * * * *